United States Patent [19]

Kessler et al.

[11] Patent Number: 5,283,178

[45] Date of Patent: Feb. 1, 1994

[54] METHOD OF FORMING AGGLUTINATES IN BLOOD SAMPLES

[75] Inventors: Marsha A. Kessler, Chicago; Patricia L. Prewitt, Ingleside, both of Ill.

[73] Assignee: Abbott Laboratories, Abbott Park, Ill.

[21] Appl. No.: 964,463

[22] Filed: Oct. 15, 1992

Related U.S. Application Data

[63] Continuation of Ser. No. 346,674, May 3, 1989, abandoned.

[51] Int. Cl.$^5$ .................... G01N 33/08; G01N 33/536
[52] U.S. Cl. .................... 435/7.25; 435/967; 436/520; 436/536; 436/538; 436/805; 424/11; 356/39
[58] Field of Search ............... 435/7.25, 967; 436/520, 436/536, 538, 805; 424/11; 356/39

[56] References Cited

U.S. PATENT DOCUMENTS

| | | | |
|---|---|---|---|
| 3,432,268 | 3/1969 | Unger | 424/11 |
| 3,488,156 | 1/1970 | Good et al. | |
| 3,574,064 | 4/1971 | Binnings et al. | |
| 4,088,448 | 5/1978 | Lilja et al. | |
| 4,152,390 | 5/1979 | Nosco et al. | |
| 4,197,088 | 4/1980 | Meserol et al. | |
| 4,290,997 | 9/1981 | Suovaniemi | 422/63 |
| 4,373,931 | 2/1983 | Takekawa | |
| 4,457,894 | 7/1984 | Clark et al. | 422/73 |
| 4,528,159 | 7/1985 | Liston | |
| 4,596,695 | 6/1986 | Cottingham | |
| 4,661,460 | 4/1987 | Sakuma | 436/165 |
| 4,727,033 | 2/1988 | Hijikata et al. | 436/69 |
| 4,737,464 | 4/1988 | McConnell et al. | |

OTHER PUBLICATIONS

Crookston "Chapter 93 Blood Typing and Cross--Matching Procedures for Blood Transfusion" in Manual of Clinical Laboratory Immunology, pp. 601-608 (1986).
Mish et al., *Webster's Ninth Callegiate dictionary* pp. 1020 & 1235 Merriam-Webster Inc. Springfield, Mass. 1990.
Chapter Eight of the *Technical Manual of the American Association of Blood Banks, Ninth Edition* (1985).
Chapter Nine, "The Rh systems", of the *Technical Manual of the American Association of Blood Banks*, Ninth Edition (1985).
Directions for Use of thr Micro-U (reg. mark) Enhancement Reagent (Low Ionic) for Antibody Detection Tests in Microplates (1986).
Selection of Methods and Instruments for Blood Banks, American Association of Blood Banks, 1987, Chapter 4 "Automation of Red Cell Testing", Ellisor, pp. 35-49.
Laboratory Medicine, vol. 16, Dec. 1985, "Automation in Immunohematology", Steven Sosler.

*Primary Examiner*—David Saunders
*Assistant Examiner*—Carol E. Bidwell
*Attorney, Agent, or Firm*—James L. Wilcox; Priscilla E. Porembski; Frank S. Ungemach

[57] ABSTRACT

The type of a blood specimen is determined by adding a portion thereof, either a diluted solution of its red cells or a portion of its plasma, to each of a multiplicity of wells in a transparent tray, by adding a blood type specific reagent to each of the wells in the tray, different reagents being added to different ones of the wells of the tray, periodically tilting the tray at a substantial angle of at least approximately 50° to opposite sides of a horizontal position to enhance any agglutination reaction which may be developing within any of the wells of the tray as a result of a match between the reagent and a blood type characteristic antigen or antibody in the portion of the blood specimen, and sensing each of the wells of the tray for the presence of an agglutinate therein by directing a light source through the wells, preferably from below the tray, a well with an agglutinate therein allowing more light from the light source to pass through the center thereof than a well without such an agglutinate therein. The agglutination enhancement technique of such blood specimen typing method is also applicable to other blood testing methods which rely on an agglutination reaction.

58 Claims, 3 Drawing Sheets

METHOD OF FORMING AGGLUTINATES IN BLOOD SAMPLES

This application is a continuation of application Ser. No. 346,674, filed May 3, 1989, which is now abandoned.

BACKGROUND OF THE INVENTION

1. Field Of The Invention

This invention relates to a method of forming agglutinates in blood samples to permit diagnostic test procedures to be performed on such blood samples. This invention also relates to a non-centrifugal method of typing samples of blood based on the formation of agglutinates in certain of the samples and the determination if agglutinates are present or absent in the samples.

2. Description Of The Prior Art

Blood typing is a form of testing which must be performed by blood banks on all donated blood to ensure that each recipient of blood will be provided with blood that is compatible with the recipient's own blood type. The blood typing reactions which must be performed on donated blood include reactions for the various blood types within the ABO System, and reactions for the various blood types within the Rh System, Systems which are described, respectively, in Chapters 8 and 9 of the Technical Manual of the American Association of Blood Banks, Ninth Edition (1985).

While manual techniques for blood typing are known, including a technique in which reactants are combined on a glass slide or a porcelain tile and are rocked back and forth by hand, or are combined on a heated apparatus frequently referred to as an Rh view box, it is also known hat it is desirable to mechanize blood typing whenever and to the maximum feasible extent, including ABO and Rh typing, as is explained in a publication entitled "Automation of Red Cell Testing" by Sandra S. Ellisor, which appears as Chapter 4 in a publication entitled "Selection of Methods and Instruments For Blood Banks," American Association of Blood Banks (1987). However, as is pointed out in this publication, the mechanical systems for red cell testing which were studied by the author were quite expensive, many involving the need for centrifugation of samples during typing. More information regarding the state of the art in the mechanization of blood typing by blood banks is contained in an article entitled "Automation in Immunohematology" by Steven D. Sosler, which appeared in the December 1985 edition of "Laboratory Medicine." Moreover, and while not set forth in any of the foregoing references, it is known that mechanized blood typing techniques lack sensitivity in typing Rh negative samples, a factor which usually requires manual re-testing of Rh negative samples, which represents approximately 15% of the United States population, and usually with the washing of the tray and the use of secondary reagents, to differentiate Du positive samples from Du negative samples.

SUMMARY OF THE INVENTION

According to the present invention there is provided a highly reliable and relatively simple method of forming agglutinates in blood samples for use, for example, in typing blood samples for a wide variety of blood types within the ABO and Rh Systems and without the need to centrifuge any of the blood samples during typing. Blood typing according to the present invention involves agglutination reactions between antigens or antibodies which are characteristic of various blood types and blood type specific reagents which are selected for reaction with specific antigens. The blood samples in the form of twice diluted red cells or undiluted plasma, reagents and, in certain cases, certain enhancement compositions are placed in individual wells in a tray, which is initially positioned in a horizontal plane, and, preferably after vibratory agitation to enhance reaction, are allowed to incubate for a predetermined period of time. The purpose of the incubation is to allow agglutinates to form in the wells in which the blood type of the sample therein is such that an antigen or antibody in such blood type will so react with the reagent therein, and the agglutination reaction is further enhanced by periodically bi-directionally tilting the tray from the horizontal position by approximately at least 50°, first to one side of the horizontal and then to the other, with a dwell for a finite period of time in each tilted position, and preferably repeatedly bi-directionally tilting the tray with at least one dwell in the horizontal position after the first bi-directional tilting sequence. The bi-directional tilting of the tray with a dwell in each tilted position has the effect of causing the agglutinates, which form at the bottoms of the wells and which are generally crescent-shaped, to repeatedly fold over on themselves, thereby absorbing smaller agglutinates which have formed in the wells, to thereby enhance the size of the largest agglutinate in the well.

Typically, agglutinates will form in two or more of the wells which contain samples from the same donor, and the pattern of the formation of agglutinates in various of the wells will identify the blood type of the donor. The detection of an agglutinate in a cell can be done by the naked eye or, preferably, by an electro optical reader which detects the presence of an agglutinate in the well by variations in the optical characteristics of the contents of the well between a well which contains one or more agglutinates and a well which does not contain any agglutinates and which thus, has the red cells of the original sample still in suspension. Each well can be rather small, initially being provided with a blood sample of only approximately 30–50 microliters in a solution of only approximately 100 microliters, and the tray is manufactured from a transparent material, such as polystyrene, and is electro-optically read for the presence of agglutinates in its wells through the bottom to minimize variation in beam size at the detector due to the meniscus effect at the top of the contents of each well. The meniscus effect, which can vary in magnitude from sample to sample, is, thus, minimized by positioning it last in the sequence of surfaces which must be traversed by the light as it passes from the light source to the detector, since all of the other surfaces in the sequence are substantially more uniform in their optical properties. The method of the present invention has a high degree of reliability, as measured by a low "No Type Determined" rate without repeated runs, in relationship to prior art mechanical blood typing systems, in spite of the fact that many of them require centrifugation during blood typing or manual visual confirmation of certain tests.

Accordingly, it is an object of the present invention to provide an improved method of performing diagnostic test procedures on blood samples. More particularly, it is an object of the present invention to provide an improved method of typing samples of blood. Even more particularly, it is an object of the present invention to provide a method of typing samples of blood which can be performed mechanically and which does not require manual re-testing of Rh negative samples. It is also an object of the present invention to provide a method for enhancing an agglutination reaction of the type used in various blood testing techniques.

For a further understanding of the present invention and the objects thereof, attention is directed to the drawing and the following brief description thereof, to the detailed description of the preferred embodiment and to the appended claims.

DETAILED DESCRIPTION OF THE PREFERRED EMBODIMENT

Figure 1:
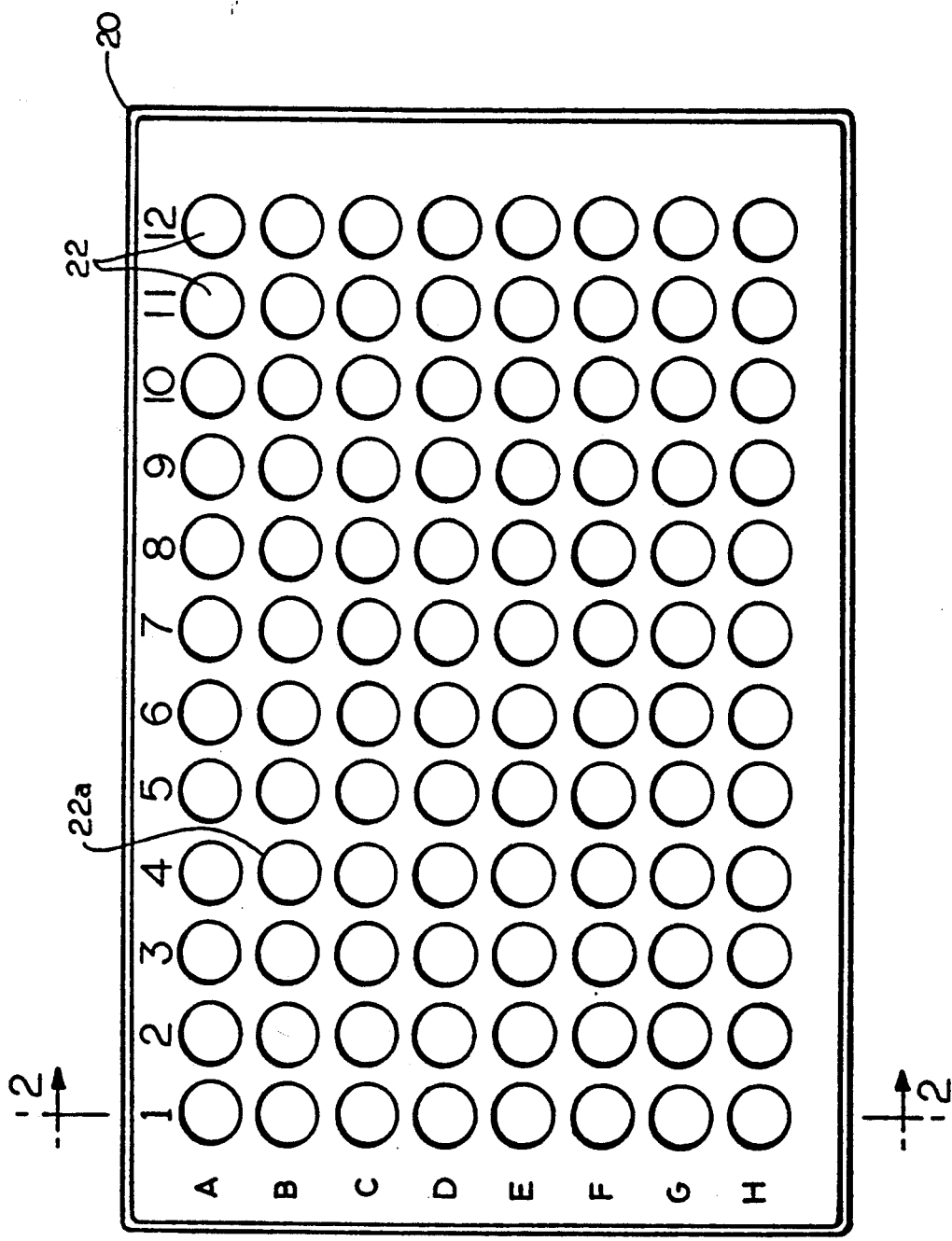
FIG. 1 is a perspective view of a multi-cell blood typing tray of a type which is used in the practice of the present invention.
Figure 3:
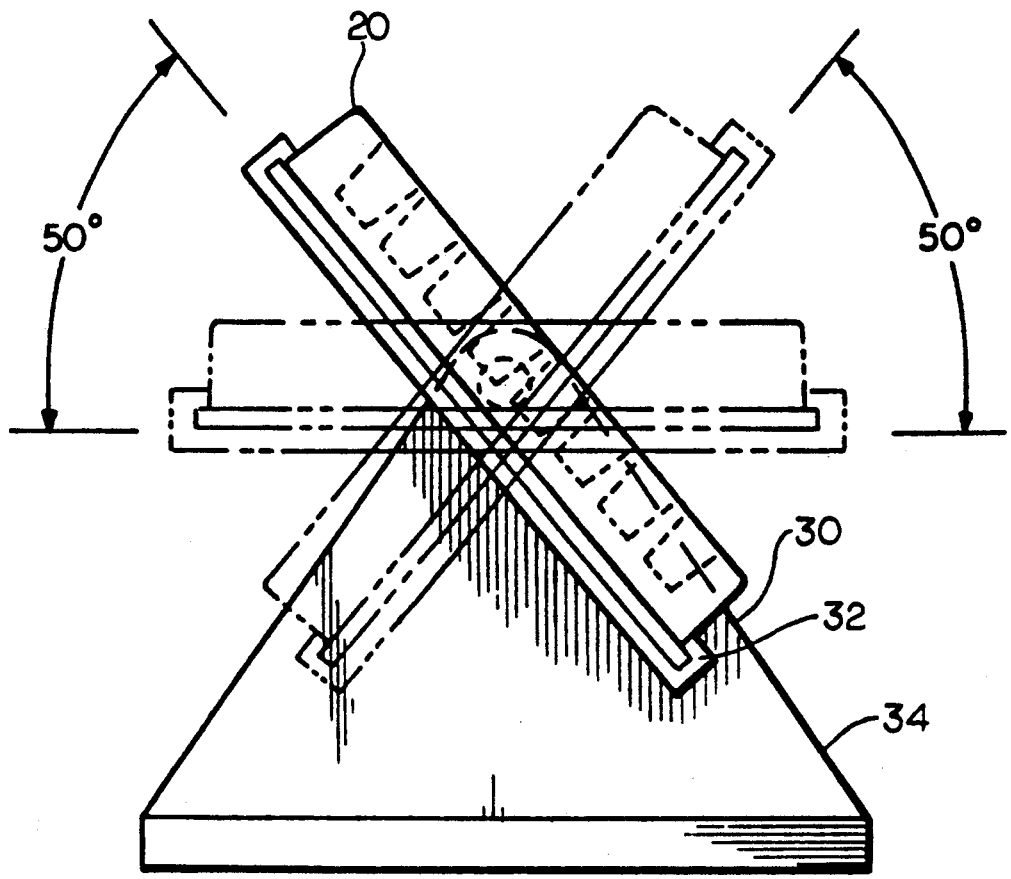
FIG. 3 is an elevational view of a tray holding device which is used in holding the tray of FIGS. 1 and 2 in the practice of the present invention.
Figure 2:
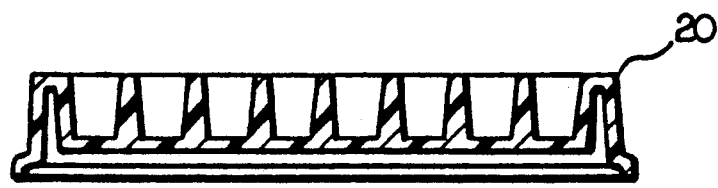
FIG. 2 is a cross-sectional view taken on line 2-2 of FIG. 1.

FIG. 1 illustrates a conventional blood typing tray 20 which is formed from a transparent thermoplastic material, for example, crystalline polystyrene, and which is provided with a multiplicity of generally cylindrical wells 22 which are arranged in an array of eight rows across, letters A-H inclusive, by a column of twelve deep in each row, numbers 1-12, inclusive. (Actually, each of the wells 22 is frustoconical with a slightly tapering sidewall to facilitate the removal of the tray from the molding tooling used in its manufacture.) Each of the wells 22 is relatively small, having an internal volume of only approximately 300 microliters, and preferably each of the wells has a generally flat bottom and a depth which is at least as great as its diameter. To help to identify a particular well 22 in the tray 20, for example, a well 22a, which is the fourth well in the second row, such well may be referred to by its position in the tray 20 as well B4.

A diluted sample of red cells or an undiluted sample of plasma, which are obtained from the donated blood sample of a given donor following the centrifugation of such blood sample, is added by pipetting to a number of the twelve wells in a given row equal to the number of tests to be run. Preferably each sample is added to its well in the tray by pipetting a fixed volume of the sample into the well, for example, approximately 35 microliters of twice diluted red cells with a red cell concentration of approximately 2-3% in a bromelain saline diluent, or approximately 30 microliters of undiluted plasma. Similarly, samples from each of up to seven other donors are added to the wells in each of the other seven rows of the tray 20, although in some cases it is desirable to add samples from one or more control specimens to the wells in one or more of the rows, typically samples from two control specimens, one each to the wells in a given row, as a "control" to verify the accuracy of the readings of the samples in the wells of the other rows. A blood type specific reagent is added by pipetting to each of the eight wells 22 across in each column of wells; similarly, a second blood type specific reagent is added to each of the eight wells 22 across in each column of wells, and so on until the sample in each well has a blood type specific reagent mixed therewith, and each reagent is added to each of the eight wells in a given row either before the addition of a sample thereto or subsequently thereto according to conventional practices. The various reagents are selected based on their ability to form agglutinates as a result of a match between a particular reagent and an antigen or antibody which is characteristic of a specific blood type within the ABO or Rh Systems, and the formulation of an agglutinate within certain of the twelve wells in each of the eight rows of wells during a dwell interval, which is frequently referred to as incubation, will identify the blood type of the source of the samples within such row of wells. Further, the agglutination reaction may be enhanced by the addition, by pipetting, of an enhancement solution, such as a high molecular weight polycation which is sold under the brand name polyvinylpyrrolidone to some or all of the wells to enhance any agglutination reaction which may be developing therein.

The formation of agglutinates within the wells 22, as heretofore described, and preferably after vibrating the tray to accelerate the start of the agglutination reaction, may be enhanced in its quickness and in the formation of an agglutinate of sufficient size to be detectable visually or electro-optically by periodically tilting the tray 20 about its longitudinal central axis, preferably by an angle of at least approximately 50° from each side of a horizontal position, with a dwell period after each movement of the tray during the incubation period. The agglutinate which forms within a well where a positive reaction is occurring will be generally crescent-shaped and will form at the bottom of the well since it will be more dense than the solution within the well, and predominantly at the juncture or corner of the bottom and the side of the well due to surface tension and/or the tilted orientation of the tray, since a corner of each well 22 with a flat bottom will be positioned below all other positions of the well in a tilted orientation of the tray 20. Thus, the tilting of the tray will cause an initially small agglutinate, which will tend to be crescent-shaped, to fold over on itself by gravity as it moves to the opposite side of the well and in the process it will absorb smaller agglutinates which are forming within the well and thereby increase in size and will reduce the number of red cells in suspension in the sample in the well, and this will increase the light transmittance capability of the sample in the central portion of the well.

Tilting of the tray 20 is accomplished by placing it in a holder 30 which is provided with a generally flat top portion 32 that is pivotal with respect to a fixed base portion 34, the tray 20 being positioned with its major longitudinal axis, that is, its axis which extends parallel to each of the eight rows of twelve wells, parallel to the tilting axis of the top portion 32 of the tray holder 30. The tray 20 is initially positioned in a horizontal position, either in the holder 30 or separately thereupon, while the blood samples for each test to be run, red cell solutions or plasma, as the case may be, are pipetted into the wells 22 of the tray 20 and the appropriate reagents and enhancement compositions, if any, are also pipetted into the wells 20, either before or after the pipetting of the samples, according to conventional practices.

Figure 4:
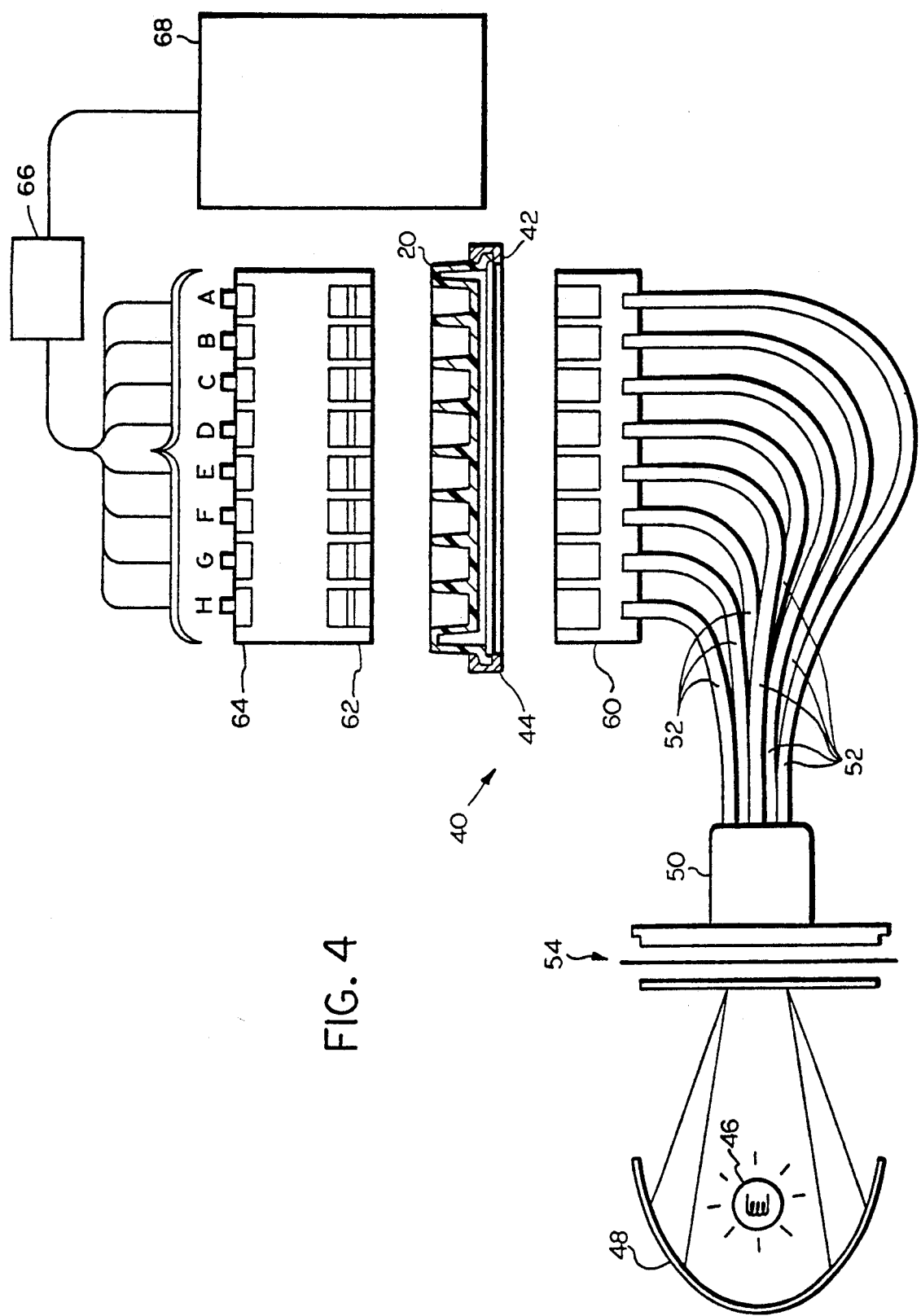
FIG. 4 is a schematic view of an electro optical reader which is used in reading the individual cells of the tray of FIG. 1 in the practice of the present invention.

Thereafter, preferably after vibrating of the tray 20 at a high frequency, for example, at a frequency of approximately 70,000 cycles per second, and for a finite period of time, for example, approximately 2 to 5 seconds, to ensure good mixing between the samples and the reagents, the tray 20, which must now be in the holder 30, is tilted in a first direction with respect to the horizon by pivoting the flat top portion 32 of the holder 30 with respect to the base portion 34 by at least approximately 50°, specifically to position the corner of each well 22 below all other portions of such well, and is maintained in such tilted position for approximately 4½-5 minutes. Thereupon the tray 20 is tilted in the opposite direction by approximately 50° for approximately 4½-5 minutes, again to position a corner of a different portion of each well 22 below all other portions of such well, it is tilted back in the first direction to an angle of approximately 65° for approximately 4½-5 minutes, it is placed in an untilted, horizontal position for approximately 4½-5 minutes, it is tilted back in the second tilted direction an angle of approximately 50° for approximately 4½-5 minutes, it is placed in an untilted, horizontal position for approximately 4½-5 minutes, it is tilted in the first tilted direction to an angle of approximately 50° for approximately 4½-5 minutes and then it is transferred to an electro-optical reading station, indicated generally by reference numeral 40 in FIG. 4, for detection of agglutinates in those wells having agglutinates therein by the variations in the optical characteristics between those wells having agglutinates therein and those wells not having agglutinates therein. The reading, which takes only 1 second for each well, or about 15 seconds for a tray when 8 wells across are done simultaneously, is done through the center of each well, and the light transmittance through a well with an agglutinate will be much higher than the light transmittance through a well without one or more agglutinates therein. This is so since the red cells in a well with an agglutinate will have been largely incorporated in one or more agglutinates which form at the sides of the well, away from the path of light transmittance, whereas in a well without an agglutinate the red cells will remain dispersed in the sample and will decrease light transmittance through the well. Thus, the total cycle time will be approximately 30-35 minutes. The use of at least one dwell in the horizontal position after the first bi-directional tilting sequence appears to be beneficial by allowing any agglutinate or agglutinates in a well to settle to the bottom thereof, which enhances the folding over of any such agglutinate in a subsequent bi-directional tilting sequence and, thus, the sweeping of the red cells and small agglutinates in the well by larger agglutinates.

The electro-optical reading station 40 has a pair of spaced apart rails 42 and 44 for supporting a tray 20, which is shown in a horizontal position, a tungsten halogen lamp 46 for producing a source of illumination, a parabolic reflector 48 for directing illumination from the lamp 46 toward a fiber optic bundle 50 which has a plurality of individual fiber optic strands 52, each of which can be in the form of an individual bundle of multiple strands, leading therefrom, an optical band pass filter system indicated generally by reference numeral 54 being provided between the lamp 46 and the fiber optic bundle to limit the wavelength of the light received by the fiber optic bundle 50 to a range of 400-600 nanometers (nm). The light which passes through the fiber optic strands 52 is transmitted into a row of wells 22 through an imaging lens device 60, and preferably into the center of each of the wells 22 through the bottoms of the wells to minimize reading errors due to the meniscus of the sample in the well. A second imaging lens device 62 above the level of the tray 20 in the reading station 40 receives the light passing through the wells being read and, in turn, passes the light to a light detector 64 which converts the light to an electronic signal. The electronic signal for each from the light detector 64 is amplified by an amplifier 66, and, as amplified, is read by a reader 68.

The digital signal from a given well 22 of the tray 20 will indicate the supernatent transmittance of the sample in the well, and this will be a function of the degree of completion of an agglutination reaction and the position of a settled agglutinate in a well, which will gravitate to a corner of the well by gravity resulting from the tilting of the tray 20 and/or by surface tension and which, therefore, will allow significant illumination to pass through the well, a characteristic that, represents a "positive" reading, as opposed to a "negative" reading in which significantly less illumination passes through the well due to the presence of unagglutinated blood cells in a suspension dispersed throughout the well being read.

The digital output from each well is multiplied by a predetermined factor, which is proportional to the full signal output from that well, to normalize the various wells which are being read to one another. Differences in donor plasma that are unrelated to blood type may be obviated at this time by adding a control reagent in one of the plasma containing wells in each row to control for sample variables which are unrelated to blood type.

The reader 68 is programmed to indicate that the sample in a well being read has read either "positive" or "negative" based on a statistical analysis of the digital readings which it receives according to a Separation Coefficient (SC), which is defined as:

$$SC = \frac{(Xp - 2SDp) - (Xn + 2SDn)}{SDp + SDn}$$

where:
Xp = positive population mean
Xn = negative population mean
SDp = standard deviation of the positive population
SDn = standard deviation of the negative population,
and cuts off between a positive reading and a negative reading according to a cutoff (CO) wherein:

CO = Xp − SDp (2+SC)

While the testing of many blood types according to the method of the present invention utilizes specimens and reagents which are conventional in prior art blood typing methods, the method of the present invention is especially effective for detection of the Du phenotype which, in known prior art methods, due to its weak reactivity, requires centrifugation of the sample being tested and washing of the test tray, and in many cases the addition of a second antibody reagent, factors which inhibit the mechanization of the testing method. According to the present invention a biotinylated anti-D agent is added, by pipetting, to the sample being tested, followed by the addition of a second anti-biotin antibody thereto. Since biotin is not normally found in human blood, no washing is needed before adding the second antibody thereto. The anti-biotin links red cells of the Du phenotype, which have been sensitized with biotinylated anti-D, so that agglutination can occur without the need for centrifugation.

In relation to known prior art blood typing methods, the method of the present invention is more sensitive, it does not require centrifugation of the sample being typed (as opposed to centrifugation of the original blood specimen to separate it into red cell and plasma components), which simplifies the mechanization of the method, it minimizes donor-to-donor variations not related to blood type, and it can be used to perform Du testing without the need for washing, centrifugation and visual confirmation. Further, use of the cutoff (CO) to classify readings as either "positive" or "negative", as heretofore described, results in increased reliability for borderline samples between the readings classified as "positive" and those classified as "negative", which adds to the reliability of the process and reduces the number of "No Type Determined" readings each of which requires reprocessing of the sample. The method also permits mechanization of blood typing without requiring manual re-testing of Rh negative samples to differentiate Du positive samples from Du negative samples.

While the method of the present invention involves an agglutination reaction enhancement technique which has been specifically described in relation to a blood typing system, it is known that other blood testing procedures, for example, testing for syphilis and testing for HIV (AIDS virus) may also involve agglutination reactions, and it is contemplated that the agglutination enhancement technique of the blood typing method of the present invention is adaptable to other blood testing procedures which utilize an agglutination reaction.

Although the best mode contemplated by the inventors for carrying out the present invention as of the filing date hereof has been shown and described herein, it will be apparent to those skilled in the art that suitable modifications, variations, and equivalents may be made without departing from the scope of the invention, such scope being limited solely by the terms of the following claims.

What is claimed is:

1. An agglutination method for determining a blood type performed on a sample obtained from a blood specimen, wherein said sample is not subjected to centrifugal forces during said method comprising the steps of:
    providing a tray having a well therein;
    transferring a finite amount of sad sample to said well;
    adding a blood typing reagent to said sample in said well;
    mixing the contents of said well to form a suspension;
    tilting said ray in a first given direction to a first inclined position at a first substantial angle with respect to a horizontal position;
    incubating said suspension at said first inclined position for a first finite period of time sufficient to form an agglutinate as the result of reaction of blood type antigen or antibody present in said sample with said blood typing reagent wherein said agglutinate accumulates at the lowest portion of said well but non-agglutinated components remain in suspension;
    tilting said tray in a second gi en direction to a second inclined position at a second substantial angle with respect to a horizontal position;
    incubating said suspension at said second inclined position for a second finite period of time sufficient for said agglutinate to accumulate at the lowest portion of said well but for non-agglutinated components to remain in suspension; and
    determining the presence of said agglutinate in said well by electrooptically measuring light transmittance through said well wherein said light transmittance through a well having agglutinate present therein is higher than the light transmittance through a well without agglutinate having test components remaining in suspension.

2. The method according to claim 1, wherein electrooptically measuring light transmittance through said well comprises the steps of:
    directing a light source through said well;
    receiving the light which passes from said light source through said well;
    comparing said light to a predetermined standard to determine the presence of said agglutinate in said well.

3. The method according to claim 2 wherein said tray is formed from a transparent material and wherein said light source is directed through said well from a light source beneath the bottom of said tray to minimize variations in the optical characteristics of said light which passes through said well due to the meniscus of the suspension therein.

4. The method according to claim 3 wherein said transparent material is crystalline polystyrene.

5. The method according to claim 4 wherein each of said first substantial angle and said second substantial angle is at least approximately 50°.

6. The method according to claim 1 wherein said second inclined position is opposed to said first inclined position.

7. The method according to claim 1, wherein the step of mixing the contents of said well to form a suspension is accomplished by subjecting said tray to high frequency vibrations for a finite period of time.

8. The method according to claim 1 wherein each of said first finite period of time and said second finite period of time is at least approximately 4½–5 minutes.

9. The method of claim 8, wherein each of said first finite period of time and said second finite period of time is approximately 4.5 minutes.

10. The method according to claim 1, wherein after incubating said suspension at said second inclined position for said second finite period of time but before determining the presence of said agglutinate in said well, said method further comprises the steps for:
    tilting said tray in said first given direction to a third inclined position at a third substantial angel with respect to a horizontal position; and
    incubating said suspension at said third inclined position for a third finite period of time sufficient for said agglutinate to accumulate at the lowest portion of said well but for non-agglutinated components to remain in suspension.

11. The method according to claim 10 wherein said third substantial angle is at least approximately 65°.

12. The method according to claim 10, wherein after incubating said suspension at said third inclined position for said third finite time but before determining the presence of said agglutinate in said well, said method further comprises the steps of:
    positioning said tray in a substantially horizontal position;
    maintaining said tray in said substantially horizontal position for a fourth finite period of time;

tilting said tray in said first given direction or said second given direction to a fourth inclined position at a fourth substantial angle with respect to a horizontal position for a fifth finite period; and incubating said suspension at said fourth inclined position sufficient for said agglutinate to accumulate at the lowest portion of said well but for non-agglutinated components to remain in suspension.

13. The method according to claim 12 wherein said fourth substantial angle is at least approximately 50°.

14. The method according to claim 12, wherein after incubating said suspension in said fourth inclined position but before determining the presence of said agglutinate in said well, said method further comprises the steps of:

positioning said tray in a substantially horizontal position;

maintaining said tray in said substantially horizontal position for a sixth finite period of time.

15. The method according to claim 14 wherein said fifth substantial angle is at least approximately 50°.

16. The method according to claim 14, wherein after maintaining said tray in said substantially horizontal position for said sixth finite period of time but before determining the presence of said agglutinate in said well, said method further comprising the steps of:

tilting said tray in the other of said first given direction or second given direction to a fifth inclined position at a fifth substantial angle with respect to a horizontal position; and incubating said suspension at said fifth inclined position for a seventh finite period of time sufficient for said agglutinate to accumulate at the lowest portion of said well but for non-agglutinated components to remain in suspension.

17. The method according to claim 14 wherein each of said first finite period of time, said second finite period of time, said third finite period of time, said fourth finite period of time, said fifth finite period of time, said sixth finite period of time and said seventh finite period of time is at least approximately 4½ minutes.

18. The method of claim 17, wherein each of said first finite period of time, said second finite period of time, said third finite period of time, said fourth finite period of time, said fifth finite period of time, said sixth finite period of time and said seventh finite period of time is approximately 4.5 minutes.

19. The method according to claim 1 wherein said well is generally cylindrical in configuration and has a depth which is at least as great as its diameter.

20. The method of claim 1, wherein the blood typing reagent is added to said well prior to or simultaneously with transferring said sample to said well.

21. An agglutination method for determining a blood type, wherein said method is performed on a sample obtained from a blood specimen and wherein said sample is not subjected to centrifugal forces during said method, comprising the steps of:

providing a tray having a plurality of wells therein;

transferring a finite amount of said sample to each of a plurality of wells in said tray;

adding a different blood typing reagent to each of the plurality of wells and mixing the contents of each of the plurality of wells to form suspensions therein;

tilting said tray in a first given direction to a first inclined position at a first substantial angle with respect to a horizontal position;

incubating said tray at said first inclined position for a first finite period of time sufficient to form an agglutinate as the result of reaction of blood type antigen or antibody present in said sample with said blood typing reagent wherein said agglutinate accumulates at the least portion of each of the plurality of wells but non-agglutinated components remain in suspension;

tilting said tray in a second given direction to a second inclined position at a second substantial angel with respect to a horizontal position;

incubating said tray at said second inclined position for a second finite period of time sufficient for said agglutinate to accumulate at the lowest portion of each of the plurality of wells but for non-agglutinated components to remain in suspension; and determining the presence of said agglutinate in each of the plurality of wells by electro-optically measuring light transmittance through said each of the plurality of wells, wherein said light transmittance through a well having agglutinate present therein is higher than the light transmittance through a well without agglutinate having test components remaining in suspension.

22. The method according to claim 21, wherein electro-optically measuring light transmittance through each of the plurality of wells comprises the steps of:

directing a light source through each of the plurality of wells;

receiving the light which passes from said light source through each of the plurality of wells;

comparing said light to a predetermined standard to determine the presence of said agglutinate in each of the plurality of wells.

23. The method according to claim 22 wherein said tray is formed from a transparent material and wherein said light source is directed through said each of the plurality of wells from a light source beneath the bottom of said tray to minimize variations in the optical characteristics of said light which passes through said each of the plurality of wells due to the meniscus of the suspension therein.

24. The method according to claim 23 wherein said transparent material is crystalline polystyrene.

25. The method according to claim 21 wherein said second inclined position is opposed to said first inclined position.

26. The method according to claim 25 wherein each of said first substantial angle and said second substantial angle is at least approximately 50°.

27. The method according to claim 21, wherein said tray having a plurality of wells therein has more than two wells.

28. The method according to claim 27, wherein prior to transferring a finite amount of said sample to each of the plurality of wells in said tray, said method further comprises the steps of:

centrifuging the blood specimen to separate the red blood cells from the plasma;

preparing a red blood cell component and preparing a plasma component; and transferring a finite amount of the red blood cells component to some of the plurality of wells and transferring a finite amount of the plasma component to others of the plurality of wells.

29. The method according to claim 28, wherein the step of mixing the contents of each of the plurality of wells is accomplished by subjecting said tray to high frequency vibrations for a finite period of time.

30. The method according to claim 27, wherein the step of mixing the contents of each of the plurality of wells is accomplished by subjecting said tray to high frequency vibrations for a finite period of time.

31. The method according to claim 21, wherein after incubating said suspensions at said second inclined position for said second finite period of time but before determining the presence of said said agglutinate in said each of the plurality of wells, said method further comprises the steps of:
  tilting said tray in said first given direction to a third inclined position at a third substantial angle with respect to a horizontal position; and
  incubating said suspensions at said third inclined position for a third finite period of time sufficient for said agglutinate to accumulate at the lowest portion of said each of the plurality of wells but for non-agglutinated components to remain in suspension.

32. The method according to claim 31 wherein said third substantial angle is at least approximately 65°.

33. The method according to claim 21 wherein each of said first finite period of time and said second finite period of time is at least approximately 4½ minutes.

34. The method of claim 33, wherein each of said first finite period of time and said second finite period of time is approximately about 4.5 minutes.

35. The method according to claim 21 wherein each of said wells is generally cylindrical in configuration and has depth which is at least as great as its diameter.

36. The method according to claim 21, wherein after incubating said suspensions at said third substantial angle but before determining the presence of said agglutinate in said each the plurality of wells, said method further comprises the steps of:
  positioning said tray in a substantially horizontal position;
  maintaining said tray in said substantially horizontal position for a fourth finite period of time;
  tilting said tray in said first given direction or said second given direction to a fourth inclined position at a fourth substantial angle with respect to a horizontal position; and
  incubating said suspensions at said fourth inclined position for a fifth finite period of time sufficient for said agglutinate to accumulate at the lowest portion of said each of the plurality of wells but for non-agglutinated components to remain in suspension.

37. The method according to claim 36 wherein said fourth substantial angle is at least approximately 50°.

38. The method according to claim 36 wherein each of said first finite period of time, said second finite period of time, said third finite period of time, said fourth finite period of time, sand said fifth finite period of time is at least approximately 4½ minutes.

39. The method of claim 38, wherein each of said first finite period of time, said second finite period of time, said third infinite period of time, said fourth finite period of time, sand said fifth finite period of time is approximately 4.5 minutes.

40. The method according to claim 36, wherein after incubating said suspensions in said fourth inclined position but before determining the presence of said agglutinate in each of the plurality of wells, said method further comprises the steps of:
  positioning said tray in a substantially horizontal position;
  maintaining said tray in said substantially horizontal position for a sixth finite period of time.

41. The method according to claim 40, wherein after maintaining said tray in said substantially horizontal position for said sixth finite period of time but before determining the presence of said agglutinate in each of the plurality of wells, said method further comprises the steps of:
  tilting said tray in the other of said first given direction or second given direction to a fifth inclined position at a fifth substantial angle with respect to a horizontal position; and
  incubating said suspensions at said fifth inclined position for a seventh finite period of time sufficient for said agglutinate to accumulate at the lowest portion of each of the plurality of wells but or non-agglutinated components to remain in suspension.

42. The method according to claim 41 wherein each of said first finite period of time, said second finite period of time, said third finite period of time, said fourth finite period of time, said fifth finite period of time, said sixth finite period of time and said seventh finite period of time is at least approximately 4½ minutes.

43. The method of claim 42, wherein each of said first finite period of time, said second finite period of time, said third finite period of time, said fourth finite period of time, said fifth finite period of time, said sixth finite period of time and said seventh finite period of time is approximately 4.5 minutes.

44. An agglutination method for determining the blood type of each of a plurality of blood specimens, wherein said method is performed on samples obtained from each of the blood specimens and wherein the samples are not subjected to centrifugal forces during said method, comprising the step of:
  providing a tray having a plurality of wells therein, said wells being aligned in a plurality of rows, said plurality of rows being at least equal in number to the number of said plurality of blood specimens;
  transferring a finite amount of each of the samples obtained from the plurality of blood specimens to each of the wells in one of said plurality of rows in said tray;
  adding each of a plurality of blood typing reagents to each of the wells having samples therein and mixing the contents of each of the wells to form suspensions therein;
  tilting said tray in a first given direction to a first inclined position at a first substantial angle with respect to a horizontal position;
  incubating said tray at said first inclined position for a first finite period of time sufficient to form an agglutinate as the result of reaction between blood type antigen or antibody present tin each of the samples with each of the plurality of blood typing reagents mixed therewith, wherein said agglutinate accumulates at the lowest portion of each of the wells but non agglutinated components remain in suspension;
  tilting said tray in a second given direction to a second inclined position at a second substantial panel with respect to a horizontal position;
  incubating said tray at said second inclined position for a second finite period of time sufficient for said agglutinate to accumulate at the lowest portion of each of the wells but for non-agglutinated components to remain in suspension; and determining the presence of said agglutinate in each of the wells by electro-optically measuring light transmittance through each of the wells wherein said light transmittance through a well having agglutinate present therein is higher than the light transmittance through a well without agglutinate having test components remaining in suspension.

45. The method according to claim 4, wherein electro-optically measuring light transmittance through each of the wells comprises the steps of:

directing a light source through each of the wells;

receiving the light which passes from said light source thorough each of the wells;

comparing said light to a predetermined standard to determine the presence of said agglutinate in each of the wells wherein the presence of an agglutinate indicates the specific blood type of each of the plurality of blood specimens based on an antibody-antigen binding reactions between the specific blood typing reagent added ad the sample tested in each of the wells.

46. The method according to claim 45 wherein said tray is formed from a transparent material and wherein said light source is directed through said each of wells from a light source beneath the bottom of said tray to minimize variations in the optical characteristics of said light which passes through said each of the wells due to the meniscus of the suspension therein.

47. The method according to claim 46 wherein said transparent material is crystalline polystyrene.

48. The method according to claim 44 wherein said second including position is opposed to said first inclined position.

49. The method according to claim 48 wherein each of said first substantial angle and said second substantial angle is at least approximately 50°.

50. The method according to claim 44 wherein each of said plurality of rows has more than tow of said wells.

51. The method according to claim 50, wherein prior to transferring a finite amount of each of the samples to each of the wells in one of said plurality of rows in said tray, said method further comprises:

centrifuging each of the blood specimen to separate red blood bells from plasma;

preparing a red blood cell component and a plasma component from each of the specimens; and transferring a finite amount of the red blood cell component to some of the wells in one of said plurality of rows and transferring a finite amount of the plasma component to others of the wells, in the same row.

52. The method according to claim 44 wherein said plurality of rows are aligned parallel to one another, and wherein said tray is tilted in said first given direction and in said second given direction about an axis which extends parallel to each of said plurality of rows.

53. The method according to claim 43 wherein the number of said plurality of rows is at least one greater than the number of said plurality of blood specimens, and further comprising transferring a portion of a control composition of known type to the wells in one of said plurality of rows.

54. The method according to claim 44 wherein each of said first finite period of time and said second finite period of time is at least approximately 4½ minutes.

55. The method of claim 54, wherein each of said first finite period of time and said second finite period of time is approximately about 4.5 minutes.

56. A method according to claim 44 wherein each of the wells is generally cylindrical in configuration and has a depth which is at least as great as its diameter.

57. The method according to claim 44, wherein mixing of the contents of each of the wells to form suspensions therein is accomplished by subjecting said tray to high frequency vibrations for a finite period of time.

58. The method of claim 44, wherein a plurality of blood typing reagents are added to the wells in each of said plurality of rows prior to or simultaneously with transferring the infinite amount of each of the samples obtained form the plurality of blood specimens to each of the wells in one of said plurality of rows.

* * * * *